(12) United States Patent
Jessup et al.

(10) Patent No.: US 11,913,169 B2
(45) Date of Patent: *Feb. 27, 2024

(54) SMALL DIAMETER, HIGH STRENGTH, LOW ELONGATION, CREEP RESISTANT, ABRASION RESISTANT BRAIDED STRUCTURE

(71) Applicant: ATEX TECHNOLOGIES, INC., Pinebluff, NC (US)

(72) Inventors: Mark Wesley Jessup, Whispering Pines, NC (US); Paul Louis Van Hulle, Pinehurst, NC (US)

(73) Assignee: ATEX Technologies, Inc., Pinebluff, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 17/881,885

(22) Filed: Aug. 5, 2022

(65) Prior Publication Data

US 2022/0372700 A1 Nov. 24, 2022

Related U.S. Application Data

(63) Continuation of application No. 16/923,183, filed on Jul. 8, 2020, now Pat. No. 11,427,958, which is a
(Continued)

(51) Int. Cl.
*D07B 1/04* (2006.01)
*D07B 1/02* (2006.01)
(Continued)

(52) U.S. Cl.
CPC .............. *D07B 1/04* (2013.01); *A61L 17/105* (2013.01); *A61L 17/145* (2013.01); *A61L 27/18* (2013.01);
(Continued)

(58) Field of Classification Search
CPC .. D07B 1/025; D07B 1/04; D07B 2201/1096; D07B 2201/2006; D07B 2205/2014; D10B 2321/0211
See application file for complete search history.

(56) References Cited

U.S. PATENT DOCUMENTS

| 3,949,755 A | 4/1976 | Vauquois |
| 4,083,829 A | 4/1978 | Calundann et al. |

(Continued)

FOREIGN PATENT DOCUMENTS

| EP | 0 523 743 A1 | 1/1993 |
| JP | 05-184660 A | 7/1993 |

(Continued)

OTHER PUBLICATIONS

Steven B. Warner, Fiber Science, Prentice Hall, p. 3 (Year: 1995).
(Continued)

*Primary Examiner* — Shaun R Hurley
(74) *Attorney, Agent, or Firm* — Nelson Mullins Riley & Scarborough LLP (57) ABSTRACT

A braided structure that includes a core and a sheath is provided. The core includes a yarn formed at least in part from an aromatic polymer (e.g., an aromatic polyester/liquid crystalline polymer or an aramid polymer), and the sheath, which includes a plurality of ultra high molecular weight polyolefin yarns, is braided around the core. The sheath has an overall diameter ranging from about 60 micrometers to about 650 micrometers. Despite its small diameter, the braided structure can be creep resistant and abrasion resistant while at the same time exhibiting low elongation, a high load at break, and high stiffness. The braided structure can be used in medical applications such as sutures, load bearing (Continued)

orthopedic applications, artificial tendons/ligaments, fixation devices, actuation cables, components for tissue repair, etc.

22 Claims, 5 Drawing Sheets

Related U.S. Application Data continuation of application No. 16/369,482, filed on Mar. 29, 2019, now Pat. No. 10,745,855.

(60) Provisional application No. 62/649,906, filed on Mar. 29, 2018.

(51) Int. Cl.
*A61L 17/10* (2006.01)
*A61L 27/50* (2006.01)
*A61L 27/18* (2006.01)
*A61L 17/14* (2006.01)

(52) U.S. Cl.
CPC .............. *A61L 27/50* (2013.01); *D07B 1/025* (2013.01); *A61L 2420/08* (2013.01); *A61L 2430/02* (2013.01); *A61L 2430/10* (2013.01); *D07B 2201/1028* (2013.01); *D07B 2201/1044* (2013.01); *D07B 2201/1096* (2013.01); *D07B 2201/2006* (2013.01); *D07B 2201/2009* (2013.01); *D07B 2201/2066* (2013.01); *D07B 2205/2014* (2013.01); *D07B 2205/2042* (2013.01); *D07B 2401/201* (2013.01); *D07B 2401/2055* (2013.01); *D07B 2401/2065* (2013.01); *D07B 2501/2076* (2013.01); *D07B 2801/10* (2013.01); *D07B 2801/14* (2013.01); *D10B 2321/0211* (2013.01); *D10B 2331/042* (2013.01); *D10B 2401/06* (2013.01); *D10B 2509/00* (2013.01)

(56) References Cited

U.S. PATENT DOCUMENTS

| | | |
|---|---|---|
| 4,161,470 A | 7/1979 | Calundann |
| 4,184,996 A | 1/1980 | Calundann |
| 4,219,461 A | 8/1980 | Calundann |
| 4,256,624 A | 3/1981 | Calundann |
| 4,279,803 A | 7/1981 | Calundann |
| 4,318,841 A | 3/1982 | East et al. |
| 4,330,457 A | 5/1982 | East et al. |
| 4,337,190 A | 6/1982 | Calundann |
| 4,339,375 A | 7/1982 | Calundann et al. |
| 4,351,917 A | 9/1982 | Calundann et al. |
| 4,351,918 A | 9/1982 | Charbonneau et al. |
| 4,355,132 A | 10/1982 | East et al. |
| 4,355,134 A | 10/1982 | Charbonneau et al. |
| 4,375,530 A | 3/1983 | Hay et al. |
| 4,393,191 A | 7/1983 | East |
| 4,421,908 A | 12/1983 | East |
| 4,429,105 A | 1/1984 | Charbonneau |
| 4,434,262 A | 2/1984 | Buckley et al. |
| 4,473,682 A | 9/1984 | Calundann et al. |
| 4,522,974 A | 6/1985 | Calundann et al. |
| 4,946,467 A | 8/1990 | Ohi et al. |
| 5,204,443 A | 4/1993 | Lee et al. |
| 5,541,240 A | 7/1996 | Makhija et al. |
| 5,771,673 A | 6/1998 | Lorch |
| 10,745,855 B2 | 8/2020 | Jessup et al. |
| 11,427,958 B2 * | 8/2022 | Jessup .................... A61L 27/34 |
| 2004/0199208 A1 | 10/2004 | Foerster |
| 2004/0267316 A1 | 12/2004 | Powell et al. |
| 2005/0033362 A1 | 2/2005 | Grafton |
| 2005/0149118 A1 | 7/2005 | Koyfman et al. |
| 2006/0025818 A1 | 2/2006 | Ferguson |
| 2006/0155328 A1 | 7/2006 | Foerster |
| 2007/0196420 A1 | 8/2007 | Dwyer |
| 2010/0016891 A1 | 1/2010 | Kennedy et al. |
| 2011/0197564 A1 | 8/2011 | Zachariades et al. |
| 2012/0297746 A1 | 11/2012 | Chou et al. |
| 2013/0231700 A1 | 9/2013 | Gedet et al. |
| 2015/0032155 A1 | 1/2015 | Dreyfuss et al. |
| 2015/0152595 A1 | 6/2015 | Van Wunnik et al. |
| 2015/0258238 A1 | 9/2015 | Ferguson et al. |
| 2016/0122918 A1 | 5/2016 | Tam et al. |
| 2017/0312080 A1 | 11/2017 | Sheth et al. |
| 2019/0223868 A1 | 7/2019 | Coffey et al. |

FOREIGN PATENT DOCUMENTS

| | | |
|---|---|---|
| JP | 2005-177500 A | 7/2005 |
| JP | 2007-277793 A | 10/2007 |
| JP | 2011-019903 A | 2/2011 |
| WO | WO 2004/082724 A2 | 9/2004 |

OTHER PUBLICATIONS

International Search Report and Written Opinion for PCT/US2019/024822, dated Jul. 9, 2019, 12 pages.

Office Action issued by Japanese Patent Office in JP Application No. 2020-552014 dated Mar. 7, 2023.

Wang et al; "Enhanced wear resistance of ultra-high molecular weight polyethylene fibers by modified-graphite oxide;" *Applied Polymer Science*; Feb. 28, 2021; 18 pp.

* cited by examiner

SMALL DIAMETER, HIGH STRENGTH, LOW ELONGATION, CREEP RESISTANT, ABRASION RESISTANT BRAIDED STRUCTURE

RELATED APPLICATIONS

The present application is a continuation of U.S. patent application Ser. No. 16/923,183, entitled "Small Diameter, High Strength, Low Elongation, Creep Resistant, Abrasion Resistant Braided Structure", filed Jul. 8, 2020, which is a continuation of U.S. patent application Ser. No. 16/369,482, entitled "Small Diameter, High Strength, Low Elongation, Creep Resistant, Abrasion Resistant Braided Structure", filed Mar. 29, 2019 and granted as U.S. Pat. No. 10,745,855, which claims priority to U.S. Provisional Patent Application No. 62/649,906 having a filing date of Mar. 29, 2018, each of which is hereby incorporated by reference in its entirety.

FIELD OF THE INVENTION

The present invention relates generally to a braided structure, and, more particularly, to a small diameter braided structure that is creep resistant and abrasion resistant while at the same time having high strength and low elongation.

BACKGROUND OF THE INVENTION

Braided structures are often used in the medical field for sutures, load bearing orthopedic applications, artificial tendons/ligaments, device fixation, actuation cables, tissue repair, etc. Because of the small diameter required for many applications, other properties of the braided structure are compromised. For example, while it may be possible to develop a braided structure with a small diameter (e.g., less than 1 millimeter, such as less than about 500 micrometers), there have been difficulties in designing such a structure to also be creep resistant and/or abrasion resistant. Challenges have also arisen in developing a braided structure having a small diameter that also has low elongation and high strength.

As such, a need exists for a braided structure having a small diameter such that it is suitable for use in medical applications while at the same time having the desired mechanical properties (e.g., creep resistance, abrasion resistance, low elongation, and/or high strength).

BRIEF DESCRIPTION OF THE INVENTION

Aspects and advantages of the invention will be set forth in part in the following description, or may be obvious from the description, or may be learned through practice of the invention.

In one aspect, the present invention is directed to a braided structure that includes a core composed of a yarn, wherein the yarn includes an aromatic polymer; and a sheath braided around the core, wherein the sheath includes a plurality of ultra high molecular weight polyolefin yarns. Further, the braided structure has an overall diameter ranging from about 60 micrometers to about 650 micrometers.

In one particular embodiment, the aromatic polymer can include a liquid crystalline polymer, an aramid polymer, or a combination thereof.

In still another aspect, the sheath can include from 2 yarns to about 48 yarns or carriers and each of the plurality of yarns or carriers in the sheath can include from 1 filament to about 72 filaments.

In yet another aspect, the sheath can include at least two sheath layers.

In one more aspect, the yarn can include from about 3 filaments to about 96 filaments.

In an additional aspect, the core can include a single yarn or at least one yarn. Further, when the core includes a single yarn, it is to be understood that the core can include at least one additional yarn (e.g., the single yarn can be 2-ply where the yarn acts as a single yarn).

In one aspect, the core can have a first diameter and the sheath can have a second diameter, where the ratio of the first diameter to the second diameter ranges from about 1:12 to about 7:10.

In still another aspect, the ultra high molecular weight polyolefin can include an ultrahigh molecular weight polyethylene (UHMWPE) having a weight average molecular weight (Mw) of at least about 500,000 grams/mole (g/mol).

In yet another aspect, the braided structure can exhibit a creep of less than about 0.60 inches (about 15.2 millimeters) when subjected to a constant load of 5 pounds-force (about 22.2 Newtons) for about 15 minutes at an about 19 inch (48.3 centimeter) gage length on a horn grip. In another aspect, the braided structure can exhibit a creep of less than about 8 percent elongation after about 15 minutes.

In one more aspect, the braided structure can exhibit resistance to abrasion after cycling the braided structure 20 millimeters in a backwards direction and 20 millimeters in a forwards direction for a total of 40 cycles across a metal edge having a 1 millimeter radius with 200 grams of weight applied to the braided structure, wherein the braided structure includes less than 50 broken filaments per linear inch after cycling.

In an additional aspect, the braided structure can exhibit a load at break ranging from about 5 pounds-force (about 22.2 Newtons) to about 60 pounds-force (about 266.9 Newtons).

In one aspect, the braided structure can exhibit an extension at break ranging from about 2% to about 5.5%.

In another aspect, the braided structure can exhibit a stiffness ranging from about 10 pounds-force per inch (about 1.75 Newtons/millimeter) to about 90 pounds-force per inch (about 15.8 Newtons/millimeter).

In an additional aspect, the braided structure can exhibit an ultimate tensile strength ranging from about $8.0 \times 10^4$ pounds per square inch (about 550 megapascals) to about $3.9 \times 10^5$ pounds per square inch (about 2710 megapascals). In another aspect, the braided structure can exhibit an ultimate tensile strength ranging from about 15 grams/denier yarn to about 35 grams/denier yarn.

In still another aspect, the braided structure can include from about 10 picks per inch (PPI) to about 90 picks per inch (PPI).

In yet another aspect, the sheath yarn can include from about 0 twists per inch (TPI) to about 12 twists per inch (TPI).

In one more aspect, the core yarn can include zero twists per inch (TPI) to about two TPI.

In an additional aspect, each of the plurality of yarns in the sheath can have a linear mass density ranging from about 8 denier to about 125 denier.

In one more aspect, the yarn in the core can have a linear mass density ranging from about 8 denier to about 1110 denier.

In another aspect, the present invention is directed to a medical device, a suture, a load bearing orthopedic application, an artificial tendon, an actuation cable, a component for tissue repair, or a fixation device that includes a braided structure as set forth above.

In still another aspect, the present invention is directed to a braided structure composed of a core that includes a yarn, where the yarn includes an aromatic polymer and a sheath braided around the core, where the sheath includes a plurality of ultra high molecular weight polyolefin yarns. Further, the braided structure exhibits an ultimate tensile strength ranging from about $8.0 \times 10^4$ pounds per square inch (about 550 megapascals) to about $3.9 \times 10^5$ pounds per square inch (about 2710 megapascals). In another aspect, the braided structure can exhibit an ultimate tensile strength ranging from about 15 grams/denier yarn to about 35 grams/denier yarn.

In yet another aspect, the present invention is directed to a braided structure composed of a core that includes a yarn, where the yarn includes an aromatic polymer and a sheath braided around the core, where the sheath includes a plurality of ultra-high molecular weight polyolefin yarns. Further, the braided structure exhibits a creep of less than about 0.60 inches (about 15.2 millimeters) when subjected to a constant load of 5 pounds-force (about 22.2 Newtons) for about 15 minutes and at an about 19 inch (48.3 centimeter) gage length on a horn grip. In another aspect, the braided structure exhibits a creep of less than about 8% elongation after about 15 minutes.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally speaking, the present invention is directed to a braided structure that includes a core and a sheath. The core includes a yarn formed from an aromatic polymer (e.g., a liquid crystalline polymer, an aramid polymer, or a combination thereof), and the sheath, which includes a plurality of ultra-high molecular weight polyolefin yarns, is braided around the core. In some embodiments, the core can be a single yarn, although in other embodiments, it is to be understood that the core can include more than one yarn. The sheath has an overall diameter ranging from about 60 micrometers to about 650 micrometers. Despite its small diameter, the braided structure can be creep resistant and abrasion resistant while at the same time exhibiting low elongation, a high load at break, and high stiffness. The braided structure can be used in medical applications such as sutures, load bearing orthopedic applications, artificial tendons/ligaments, device fixation, actuation cables for medical devices, components for tissue repair, etc.

Figure 1:
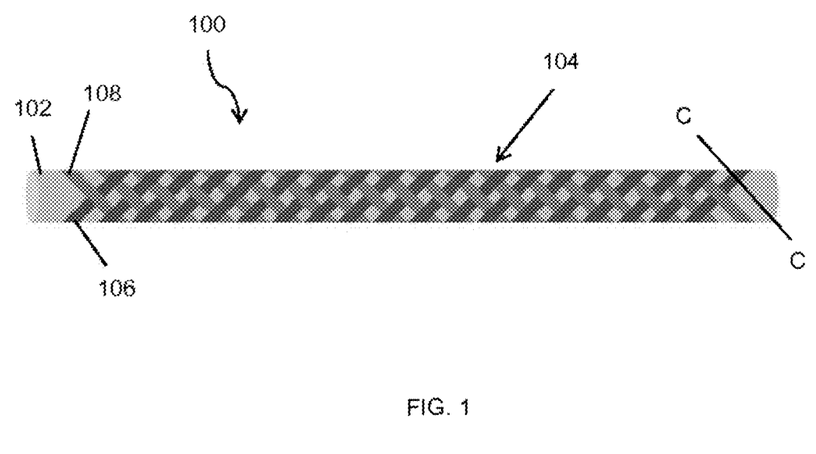
FIG. 1 illustrates a side view of a braided structure contemplated by the present invention.
Figure 2:
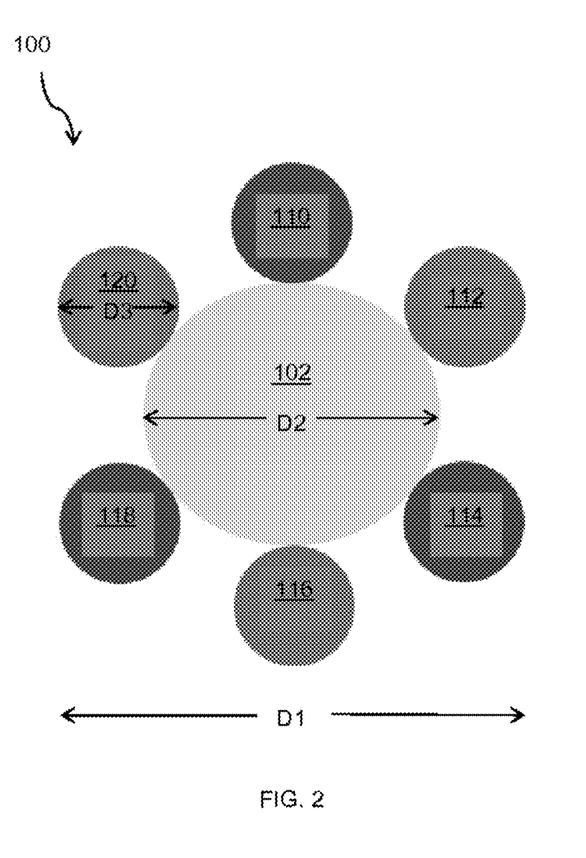
FIG. 2 illustrates a cross-sectional view of the braided structure of FIG. 1 taken at line C-C.

Referring now to the drawings, FIG. 1 illustrates a side view of a braided structure 100 contemplated by the present invention, while FIG. 2 illustrates a cross-sectional view of the braided structure 100 taken at line C-C. The braided structure 100 includes a core 102 surrounded by a sheath 104 and is braided in a 1×1 pattern. However, other braid patterns known in the art can alternatively be used (e.g., 1×2, 2×2, etc.). The core 102 can include a single strand of yarn, where the yarn can include from about 3 filaments to about 96 filaments, such as from about 4 filaments to about 84 filaments, such as from about 5 filaments to about 72 filaments, such as from about 6 filaments to about 60 filaments. In one particular embodiment as shown in FIGS. 1 and 2, the core 102 can include a single yarn. However, it is also to be understood that the core 102 can include more than a single yarn, such as at least one additional yarn, such that the core 102 can include from about 2 yarns to about 10 yarns, such as from about 2 yarns to about 8 yarns, such as from about 2 yarns to about 6 yarns, such as from about 4 yarns to about 8 yarns, such as from about 4 yarns to about 6 yarns, where the yarns can be braided or unbraided. The sheath 104 can include from 2 yarns to about 48 yarns, such as from 3 yarns to about 24 yarns, such as from about 4 yarns to about 16 yarns.

It is also to be understood that the sheath yarns and/or core yarns may contain twist or no twist or no intentional twist or unintentional twist. Yarn twist can include from 0 to 2 intentional or unintentional twists per inch, such as from 0 to 1 intentional or unintentional twists per inch, such as from 0 to 0.75 intentional or unintentional twists per inch, such as from 0 to 0.5 intentional or unintentional twists per inch, such as from 0 to 0.25 intentional or unintentional twists per inch. It is to be understood that unintentional twist may include twist that accumulates in the yarn during normal manufacturing processes. A non-limiting example of unintentional twist is twist that is obtained once the yarn is wrapped or spun on the spool.

Meanwhile, the sheath 104 can include a plurality of S yarns 106 or Z yarns 108 wrapped around the core 102. During manufacturing of a braided structure, a portion of the machine yarn carriers can move in a clockwise direction, and the other portion of the carriers can move in a counter-clockwise direction. In a non-limiting example, half of the carriers move in the clockwise direction and the other half of the carriers move in the counter-clockwise direction. As the machine carriers move around the braided structure, yarn is pulled off each carrier and gathered at the braiding point. The sheath yarn may be naturally twisted or unintentionally twisted due to the movement of the carriers around the machine. For optimal braid strength and minimal braid creep, the yarn filaments must remain close to parallel with the braided structure by using sheath yarn with S twist moving clockwise direction around the braided structure and sheath yarn with Z twist moving counter-clockwise direction around the braided structure.

In other words, the sheath yarn 104 can exhibit twist in both the S and Z directions. For instance, the sheath yarn 104 can include from 1 to about 12, such as from about 2 to about 10, such as from about 3 to about 8 S or Z yarns braided clockwise 106 and from 1 to about 12, such as from about 2 to about 10, such as from about 3 to about 8 opposing S or Z yarns braided counterclockwise 108. In other words, the sheath can include from 2 yarns to about 48 yarns, such as from about 4 yarns to about 24 yarns, such as from about 6 yarns to about 16 yarns, where half of the yarns are wrapped around the core in a clockwise direction and half of the yarns are wrapped around the core in a counterclockwise direction.

In one particular embodiment as shown in FIG. 2, the sheath 104 can include three S or Z yarns 110, 114, and 118 and three opposing S or Z yarns 112, 116, and 120. Moreover, each clockwise carrier of S, Z, or untwisted yarn 106 or counterclockwise carrier of S, Z, or untwisted yarn 108 can include from 1 filament to about 72 filaments, such as from 2 filaments to about 60 filaments, such as from about 4 filaments to about 48 filaments, such as from about 6 filaments to about 36 filaments. The overall stiffness and flexibility of the braided structure 100 can be optimized based on the number of yarn filaments. In one embodiment, increasing the number of yarn filaments can improve the abrasion resistance of the braided structure 100.

Further, the braided structure 100 can have an overall diameter D1 ranging from about 0.0024 inches to about 0.026 inches (about 60 micrometers to about 650 micrometers), such as from about 0.0057 inches to about 0.026 inches (about 145 micrometers to about 650 micrometers), such as from about 0.0085 inches to about 0.025 inches (about 215 micrometers to about 625 micrometers), such as from about 0.009 inches to about 0.024 inches (about 230 micrometers to about 600 micrometers), such as from about 0.0095 inches to about 0.023 inches (about 245 micrometers to about 575 micrometers), such as from about 0.0118 inches to about 0.016 inches (about 300 micrometers to about 400 micrometers).

Meanwhile, the core 102 can have a diameter D2 ranging from about 0.0012 inches to about 0.031 inches (about 30 micrometers to about 333 micrometers), such as from about 0.0014 inches to about 0.0046 inches (about 36 micrometers to about 116 micrometers), such as from about 0.0016 inches to about 0.0044 inches (about 40 micrometers to about 112 micrometers), such as from about 0.0018 inches to about 0.0042 inches (about 46 micrometers to about 108 micrometers), while each of the individual sheath yarns 110, 112, 114, 116, 118, and 120 can have a diameter D3 ranging from about 0.0013 inches to about 0.0060 inches (about 30 micrometers to about 152 micrometers), such as from about 0.0026 inches to about 0.0058 inches (about 66 micrometers to about 148 micrometers), such as from about 0.0024 inches to about 0.0056 inches (about 60 micrometers to about 142 micrometers), such as from about 0.0030 inches to about 0.0054 inches (about 76 micrometers to about 138 micrometers).

In one particular embodiment, the ratio of the diameter D2 of the core 102 to the diameters D3 of each of the yarns in 110, 112, 114, 116, 118, and 120 in the sheath 104 (D2:D3) can range from about 1:12 to about 7:10, such as from about 1:8 to about 2:3, such as from 1:4 to about 1:2, such as from 1:3 to about 4:10. Without intending to be limited by any particular theory, the present inventors have found that such a balance between the diameter D2 of the core 102 and the diameter D3 of each of the yarns in the sheath 104, in conjunction with other characteristics such as the materials used for the core 102 and the sheath 104, results in a braided structure 100 that has a small diameter such that it can be used as a suture or other medical application (e.g., actuation cables) without sacrificing the mechanical properties of the braided structure (e.g., creep resistance, abrasion resistance, low elongation, high strength, etc.).

In applications where a braided structure is used with, within, or in conjunction with a medical device, the material properties and mechanical properties of the core 102 and sheath 104 effect the braided structure and the overall device containing the braided structure. In one embodiment, by utilizing the balance of diameter D2 of the core 102 and the diameter D3 of the sheath 104, the preferred overall diameter of the braided structure 100 can be achieved to fit through a small designated lumen within a medical device and still met the requirements for adequate strength and creep resistance. Furthermore, a braided structure 100 containing a core 102 and sheath 104 larger than the preferred diameter range of the present invention would not fit within a designated lumen for specific medical device applications. Additionally, braided structures with tensile strength higher than the preferred range of the present invention may result in damage to the final medical device that contains a braided structure 100. Moreover, to protect the core 102 from abrasion and yarn misalignment, the diameter D2 of the core 102 and diameter D3 of the sheath 104 are selected to provide adequate sheath coverage around the core 102 with a desired picks per inch.

Moreover, the linear mass density of the core 102 and sheath 104 can also be controlled to obtain the desired properties of the braided structure. Specifically, the linear mass density of the core 102 can range from about 8 denier to about 1110 denier, such as from about 75 denier to about 125 denier, such as from about 80 denier to about 120 denier. Further, the linear mass density of each of the yarns in the sheath 104 can range from about 8 denier to about 125 denier, such as from about 25 denier to about 75 denier, such as from about 30 denier to about 70 denier, such that the overall linear mass density of the sheath 104 can also range from about 8 denier to about 125 denier, such as from about 25 denier to about 75 denier, such as from about 30 denier to about 70 denier.

Moreover, although in some embodiments the core 102 comprises a single yarn have 0 twist per inch, when a single or plurality of yarns are utilized, the core yarn 102 can have from 0 twist per inch (TPI) to about 1 TPI, such as from 0 TPI to about 2 TPI, such as from 0 TPI to about 15 TPI, such as from about 4 TPI to about 10 TPI, such as from about 5 TPI to about 9 TPI. In addition, the sheath yarn 104 can be formed so that it includes from 0 twist per inch (TPI) to about 1 TPI, such as from 0 TPI to about 2 TPI, such as from 0 TPI to about 15 TPI, 3 TPI to about 12 TPI, such as from about 4 TPI to about 10 TPI, such as from about 5 TPI to about 9 TPI. The TPI of the braided structure effects the abrasion resistance of the braided structure 100, where abrasion during manufacturing of the braided structure can be minimized without compromising the tensile strength by using the preferred TPI range of the disclosed invention. Twists may include unintentional twist obtained once the yarn is wrapped or spun on the spool or intentional twist incorporated into the yarn by a manufacturing process.

Further, the braided structure 100 can include from about 10 picks per inch (PPI) to about 90 picks per inch, such as from about 12 PPI to about 60 PPI, such as from about 14 PPI to about 40 PPI. By using the preferred PPI range, low creep, low elongation, and desired stiffness of the braided structure can be achieved. For example, a PPI greater than the preferred range can result in an undesired high creep and elongation, which, in turn, decreases the stiffness of the braided structure outside of the desired stiffness range. Moreover, utilizing a PPI lower than the preferred range can result in an undesired low creep and elongation, which, in turn, increases the stiffness of the braided structure outside of the desired stiffness range. Further, while a PPI value lower than the preferred range may result in a braided structure with minimal creep, this low PPI value may not provide adequate sheath yarn coverage around the core, which may result in poor abrasion resistance.

Based on the specific combination of sheath and core yarn characteristics described above, a small diameter braided structure having a diameter ranging from about 60 micrometers to about 650 micrometers can be formed that exhibits desired abrasion resistance, creep resistance, load at break, load at break with 180° bend, extension at break, and stiffness.

For instance, the braided structure 100 of the present invention can be abrasion resistant in that it exhibits little to no fraying. In one embodiment, the braided structure includes less than 50 broken filaments per linear inch, such as less than 25 broken filaments per linear inch, such less than 10 broken filaments per linear inch, such as less than 5 broken filaments per linear inch after cycling the braided structure 20 millimeters in a backwards direction and 20 millimeters in a forwards direction for a total of 40 cycles across a metal edge having a 1 millimeter radius with 200 grams of weight applied to the braided structure.

Further, the braided structure 100 of the present invention can exhibit a creep of less than about 0.60 inches (about 15.2 millimeters), such as less than about 0.58 inches (about 14.7 millimeters), such as less than about 0.56 inches (about 14.2 millimeters), such as less than about 0.54 millimeters (about 13.7 millimeters) when subjected to a constant load of 5 pounds-force (about 22.2 Newtons) for about 15 minutes and at an about 19 inch (48.3 centimeter) gage length on a horn grip. In one particular embodiment, the creep can range from about 0.001 inches (about 0.0025 millimeters) to about 0.25 inches (about 6.4 millimeters).

Further, the braided structure 100 of the present invention can exhibit a creep of less than about 8% elongation after about 15 minutes, such as less than about 7% elongation after about 15 minutes, such as less than about 6% elongation after about 15 minutes, such as less than about 4% elongation after about 15 minutes, such as less than about 3% elongation after about 15 minutes, such as less than about 2% elongation after about 15 minutes, such as less than about 1% elongation after about 15 minutes, such as less than about 0.5% elongation after about 15 minutes, such as less than about 0.25% elongation after about 15 minutes. In one embodiment, the braided structure 100 can exhibit a creep between about 0.2% and about 3% elongation after about 15 minutes.

In addition, when undergoing tensile testing, the braided structure 100 of the present invention can exhibit a load at break ranging from about 5 pounds-force (about 22.2 Newtons) to about 60 pounds-force (about 266.9 Newtons), such as from about 7.5 pounds-force (about 33.4 Newtons) to about 50 pounds-force (about 222.4 Newtons), such as from about 10 pounds-force (about 44.5 Newtons) to about 40 pounds-force (about 177.9 Newtons), such as from about 12.5 pounds-force (about 55.6 Newtons) to about 30 pounds-force (about 133.4 Newtons).

Further, when subjected to tensile testing, the braided structure 100 of the present invention can exhibit a load at break with an 180° bend ranging from about 10 pounds-force (about 44.5 Newtons) to about 70 pounds force (about 311.4 Newtons), such as from about 12.5 pounds-force (about 55.6 Newtons) to about 60 pounds-force (about 266.9 Newtons), such as from about 15 pounds-force (about 66.7 Newtons) to about 50 pounds-force (about 222.4 Newtons) when the braided structure is wrapped around a pin or wire having a diameter ranging from about 0.009 inches (about 229 micrometers) to about 0.015 inches (about 381 micrometers), such as about 0.012 inches (about 305 micrometers).

Moreover, when subjected to tensile testing, the braided structure 100 of the present invention can exhibit an extension or elongation at break ranging from about 2% to about 5.5%, such as from about 2.1% to about 5%, such as from about 2.2% to about 4.75%, such as from about 2.3% to about 4.5%.

Additionally, when subjected to tensile testing, the braided structure 100 of the present invention can exhibit a stiffness ranging from about 10 pounds-force/inch (about 1.75 Newtons/millimeter) to about 90 pounds-force/inch (about 15.8 Newtons/millimeter), such as from about 15 pounds-force/inch (about 2.6 Newtons/millimeter) to about 85 pounds-force/inch (about 14.9 Newtons/millimeter), such as from about 20 pounds-force/inch (about 3.5 Newtons/millimeter) to about 80 pounds-force/inch (about 14.0 Newtons/millimeter), such as from about 25 pounds-force/inch (about 4.4 Newtons/millimeter) to about 75 pounds-force/inch (about 13.1 Newtons/millimeter).

Further, when subjected to tensile testing, the braided structure can exhibit an ultimate tensile strength ranging from about $8.0 \times 10^4$ pounds per square inch (about 550 megapascals) to about $3.9 \times 10^5$ pounds per square inch (about 2710 megapascals), such as from about $1.5 \times 10^5$ pounds per square inch (about 1034 megapascals) to about $3 \times 10^5$ pounds per square inch (about 2068 megapascals), such as from about $1.6 \times 10^5$ pounds per square inch (about 1103 megapascals) to about $2.75 \times 10^5$ pounds per square inch (about 1896 megapascals), such as from about $1.7 \times 10^5$ pounds per square inch (about 1172 megapascals) to about 2.5×10$^5$ pounds per square inch (about 1723 megapascals).

In another aspect, the braided structure can exhibit an ultimate tensile strength ranging from about 15 grams/denier yarn to about 35 grams/denier yarn, such as to about 16 grams/denier yarn to about 30 grams/denier yarn, such as to about 18 grams/denier yarn to about 25 grams/denier yarn, such as to about 20 grams/denier yarn to about 25 grams/ denier yarn, such as to about 22 grams/denier yarn to about 25 grams/denier yarn.

The various components of the braided structure will now be described in more detail.

I. Core

According to the present invention, the core of the braided structure can include a single aromatic polymer yarn. For instance, the aromatic polymer can include a liquid crystalline polymer, an aramid polymer, or a combination thereof. The term "liquid crystalline polymer" or "LCP" refers to a polymer that can possess a rod-like structure that allows it to exhibit liquid crystalline behavior in its molten state (e.g., thermotropic nematic state). The polymer may contain aromatic units (e.g., aromatic polyesters, aromatic polyesteramides, etc.) so that it is wholly aromatic (e.g., containing only aromatic units) or partially aromatic (e.g., containing aromatic units and other units, such as cycloaliphatic units). The polymer may also be fully crystalline or semi-crystalline in nature. In some embodiments, suitable thermotropic liquid crystalline polymers may include, for instance, aromatic polyesters (e.g., liquid crystalline aromatic polyesters or liquid crystalline polyesters), aromatic poly(esteramides), aromatic poly(estercarbonates), aromatic polyamides, etc., and may likewise contain repeating units formed from one or more aromatic hydroxycarboxylic acids, aromatic dicarboxylic acids, aromatic diols, aromatic aminocarboxylic acids, aromatic amines, aromatic diamines, etc., as well as combinations thereof.

Aromatic polyesters, for instance, may be obtained from (1) two or more aromatic hydroxycarboxylic acids; (2) at least one aromatic hydroxycarboxylic acid, at least one aromatic dicarboxylic acid, and at least one aromatic diol; and/or (3) at least one aromatic dicarboxylic acid and at least one aromatic diol. Examples of suitable aromatic hydroxycarboxylic acids include, 4-hydroxybenzoic acid; 4-hydroxy-4'-biphenylcarboxylic acid; 2-hydroxy-6-naphthoic acid; 2-hydroxy-5-naphthoic acid; 3-hydroxy-2-naphthoic acid; 2-hydroxy-3-naphthoic acid; 4'-hydroxyphenyl-4-benzoic acid; 3'-hydroxyphenyl-4-benzoic acid; 4'-hydroxyphenyl-3-benzoic acid, etc., as well as alkyl, alkoxy, aryl and halogen substituents thereof. Examples of suitable aromatic dicarboxylic acids include terephthalic acid; isophthalic acid; 2,6-naphthalenedicarboxylic acid; diphenyl ether-4,4'-dicarboxylic acid; 1,6-naphthalenedicarboxylic acid; 2,7-naphthalenedicarboxylic acid; 4,4'-dicarboxybiphenyl; bis(4-carboxyphenyl)ether; bis(4-carboxyphenyl)butane; bis(4-carboxyphenyl)ethane; bis(3-carboxyphenyl)ether; bis(3-carboxyphenyl)ethane, etc., as well as alkyl, alkoxy, aryl and halogen substituents thereof. Examples of suitable aromatic diols include hydroquinone; resorcinol; 2,6-dihydroxynaphthalene; 2,7-dihydroxynaphthalene; 1,6-dihydroxynaphthalene; 4,4'-dihydroxybiphenyl; 3,3'-dihydroxybiphenyl; 3,4'-dihydroxybiphenyl; 4,4'-dihydroxybiphenyl ether; bis(4-hydroxyphenyl)ethane, etc., as well as alkyl, alkoxy, aryl and halogen substituents thereof. In one particular embodiment, the aromatic polyester is derived from 4-hydroxybenzoic acid and 2,6-hydroxynaphthoic acid. The monomer units derived from 4-hydroxybenzoic acid may constitute from about 45% to about 85% (e.g., 73%) of the polymer on a mole basis and the monomer units derived from 2,6-hydroxynaphthoic acid may constitute from about 15% to about 55% (e.g., 27%) of the polymer on a mole basis. The synthesis and structure of these and other aromatic polyesters may be described in more detail in U.S. Pat. Nos. 4,161,470; 4,473,682; 4,522,974; 4,375,530; 4,318,841; 4,256,624; 4,219,461; 4,083,829; 4,184,996; 4,279,803; 4,337,190; 4,355,134; 4,429,105; 4,393,191; 4,421,908; 4,434,262; and 5,541,240.

Liquid crystalline polyesteramides may likewise be obtained from (1) at least one aromatic hydroxycarboxylic acid and at least one aromatic aminocarboxylic acid; (2) at least one aromatic hydroxycarboxylic acid, at least one aromatic dicarboxylic acid, and at least one aromatic amine and/or diamine optionally having phenolic hydroxy groups; and (3) at least one aromatic dicarboxylic acid and at least one aromatic amine and/or diamine optionally having phenolic hydroxy groups. Suitable aromatic amines and diamines may include, for instance, 3-aminophenol; 4-aminophenol; 1,4-phenylenediamine; 1,3-phenylenediamine, etc., as well as alkyl, alkoxy, aryl and halogen substituents thereof. In one particular embodiment, the aromatic polyesteramide is derived from 2,6-hydroxynaphthoic acid, terephthalic acid, and 4-aminophenol. The monomer units derived from 2,6-hydroxynaphthoic acid may constitute from about 35% to about 85% of the polymer on a mole basis (e.g., 60%), the monomer units derived from terephthalic acid may constitute from about 5% to about 50% (e.g., 20%) of the polymer on a mole basis, and the monomer units derived from 4-aminophenol may constitute from about 5% to about 50% (e.g., 20%) of the polymer on a mole basis. In another embodiment, the aromatic polyesteramide contains monomer units derived from 2,6-hydroxynaphthoic acid, and 4-hydroxybenzoic acid, and 4-aminophenol, as well as other optional monomers (e.g., 4,4'-dihydroxybiphenyl and/or terephthalic acid). The synthesis and structure of these and other aromatic poly(esteramides) may be described in more detail in U.S. Pat. Nos. 4,339,375; 4,355,132; 4,351,917; 4,330,457; 4,351,918; and 5,204,443.

Meanwhile, the term "aramid polymer" refers to a class of polymers known as aromatic polyamides. Such polymers are typically prepared by the reaction between an amine group and a carboxylic acid halide group. Examples of suitable aramid polymers contemplated by the present invention include poly-metaphenylene isophthalamides and p-phenylene terephthalamides.

In one particular embodiment, the aromatic polymer can be formed into a core 102 having a single yarn with zero turns per inch that has a linear mass density ranging from about 96 denier to about 105 denier. The yarn can also include from about 36 to about 72 filaments and can have a diameter ranging from about 0.0036 inches to about 0.0041 inches (about 90 micrometers to about 105 micrometers). Further, the single yarn of the core 102 can exhibit a percent elongation (extension at break) ranging from about 2.1% to about 2.5%. In addition, the yarn can exhibit a tenacity ranging from about 21 g/denier to about 28 g/denier and can have a maximum force ranging from about 2016 grams to about 2940 grams.

In another particular embodiment, the aromatic polymer can be formed into a core 102 having a single yarn with zero turns per inch that has a linear mass density ranging from about 21 denier to about 29 denier. The yarn can also include from 2 to about 12 filaments and can have a diameter ranging from about 0.0018 inches to about 0.0022 inches (about 46 micrometers to about 56 micrometers). Further, the single yarn of the core 102 can exhibit a percent elongation (extension at break) ranging from about 3% to about 5%. In addition, the yarn can exhibit a tenacity ranging from about 20 g/denier to about 40 g/denier and can have a maximum force ranging from about 600 grams to about 950 grams.

II. Sheath

According to the present invention, the sheath of the braided structure can include a plurality of sheath yarns formed from a high molecular weight polymer, such as a high molecular weight polyolefin.

In one particular embodiment, the sheath can include a plurality of sheath yarns formed from an ultra high molecular weight polyethylene (UHMWPE) polymer that can have a weight average molecular weight (Mw) of at least about 500,000 grams/mole (g/mol). In some embodiments, the average molecular weight of the UHMWPE polymer can range from about 500,000 g/mol to about 10,000,000 g/mol, such as from about 1,000,000 g/mol to about 8,000,000 g/mol, such as from about 1,000,000 g/mol to about 6,000,000 g/mol, such as from about 2,000,000 g/mol to about 4,000,000 g/mol.

In addition, the UHMWPE polymer may be a homopolymer of ethylene or a copolymer of ethylene and at least one comonomer. Suitable comonomers that may be used to form a UHMWPE copolymer include, but are not limited to, an alpha-olefin or cyclic olefin having 3 to 20 carbon atoms. Non-limiting examples of suitable comonomers include 1-butene, 1-pentene, 1-hexene, 1-heptene, 1-octene, cyclohexene, and dienes with up to 20 carbon atoms (e.g. butadiene or 1,4-hexadiene). Comonomers may be present in the UHMWPE copolymer in an amount from about 0.001 mole % to about 10 mole %, from about 0.01 mole % to about 5 mole %, or from about 0.1 mole % to about 1 mole %.

In one particular embodiment, the sheath 104 can include 6 UHMWPE yarns having between 6 and 7 turns per inch (TPI), where each yarn has a linear mass density ranging from about 40 denier to about 60 denier so that the overall linear mass density of the sheath 104 also ranges from about 40 denier to about 60 denier. Each of the yarns in the sheath 104 can also include from about 20 to about 35 filaments and can have a diameter ranging from about 0.0030 inches to about 0.0037 inches (about 76 micrometers to about 94 micrometers). Further, each of the yarns in the sheath 104 can exhibit a percent elongation (extension at break) ranging from about 1.3% to about 7%. In addition, each of the yarns can exhibit a tenacity ranging from about 25 g/denier to about 51 g/denier and can have a maximum force ranging from about 1150 grams to about 3036 grams.

In one particular embodiment, the sheath 104 can include from 4 to 24 UHMWPE untwisted yarns, where each yarn has a linear mass density ranging from about 40 denier to about 60 denier so that the overall linear mass density of the sheath 104 also ranges from about 25 denier to about 120 denier. Each of the yarns in the sheath 104 can also include from about 16 to about 42 filaments and can have a diameter ranging from about 0.0030 inches to about 0.0052 inches (about 76 micrometers to about 132 micrometers). Further, each of the yarns in the sheath 104 can exhibit a percent elongation (extension at break) ranging from about 2% to about 5%. In addition, each of the yarns can exhibit a tenacity ranging from about 20 g/denier to about 55 g/denier and can have a maximum force ranging from about 650 grams to about 4500 grams.

In another embodiment, the yarns in the sheath 104 can include another polymer in addition to a high molecular weight polyolefin. For instance, one or more of the yarns in the sheath 104 can include a blend of the high molecular weight polyolefin and an additional polymer, or one or more of the yarns can be formed solely from the additional polymer. In one embodiment, the additional polymer can be an aromatic polymer. For instance, the aromatic polymer can include a liquid crystalline polymer, an aramid polymer, or a combination thereof. The term "liquid crystalline polymer" or "LCP" refers to a polymer that can possess a rod-like structure that allows it to exhibit liquid crystalline behavior in its molten state (e.g., thermotropic nematic state). The polymer may contain aromatic units (e.g., aromatic polyesters, aromatic polyesteramides, etc.) so that it is wholly aromatic (e.g., containing only aromatic units) or partially aromatic (e.g., containing aromatic units and other units, such as cycloaliphatic units). The polymer may also be fully crystalline or semi-crystalline in nature. In some embodiments, suitable thermotropic liquid crystalline polymers may include, for instance, aromatic polyesters (e.g., liquid crystalline aromatic polyesters or liquid crystalline polyesters), aromatic poly(esteramides), aromatic poly(estercarbonates), aromatic polyamides, etc., and may likewise contain repeating units formed from one or more aromatic hydroxycarboxylic acids, aromatic dicarboxylic acids, aromatic diols, aromatic aminocarboxylic acids, aromatic amines, aromatic diamines, etc., as well as combinations thereof.

Aromatic polyesters, for instance, may be obtained from (1) two or more aromatic hydroxycarboxylic acids; (2) at least one aromatic hydroxycarboxylic acid, at least one aromatic dicarboxylic acid, and at least one aromatic diol; and/or (3) at least one aromatic dicarboxylic acid and at least one aromatic diol. Examples of suitable aromatic hydroxycarboxylic acids include, 4-hydroxybenzoic acid; 4-hydroxy-4'-biphenylcarboxylic acid; 2-hydroxy-6-naphthoic acid; 2-hydroxy-5-naphthoic acid; 3-hydroxy-2-naphthoic acid; 2-hydroxy-3-naphthoic acid; 4'-hydroxyphenyl-4-benzoic acid; 3'-hydroxyphenyl-4-benzoic acid; 4'-hydroxyphenyl-3-benzoic acid, etc., as well as alkyl, alkoxy, aryl and halogen substituents thereof. Examples of suitable aromatic dicarboxylic acids include terephthalic acid; isophthalic acid; 2,6-naphthalenedicarboxylic acid; diphenyl ether-4,4'-dicarboxylic acid; 1,6-naphthalenedicarboxylic acid; 2,7-naphthalenedicarboxylic acid; 4,4'-dicarboxybiphenyl; bis(4-carboxyphenyl)ether; bis(4-carboxyphenyl)butane; bis(4-carboxyphenyl)ethane; bis(3-carboxyphenyl)ether; bis(3-carboxyphenyl)ethane, etc., as well as alkyl, alkoxy, aryl and halogen substituents thereof. Examples of suitable aromatic diols include hydroquinone; resorcinol; 2,6-dihydroxynaphthalene; 2,7-dihydroxynaphthalene; 1,6-dihydroxynaphthalene; 4,4'-dihydroxybiphenyl; 3,3'-dihydroxybiphenyl; 3,4'-dihydroxybiphenyl; 4,4'-dihydroxybiphenyl ether; bis(4-hydroxyphenyl)ethane, etc., as well as alkyl, alkoxy, aryl and halogen substituents thereof. In one particular embodiment, the aromatic polyester is derived from 4-hydroxybenzoic acid and 2,6-hydroxynaphthoic acid. The monomer units derived from 4-hydroxybenzoic acid may constitute from about 45% to about 85% (e.g., 73%) of the polymer on a mole basis and the monomer units derived from 2,6-hydroxynaphthoic acid may constitute from about 15% to about 55% (e.g., 27%) of the polymer on a mole basis. The synthesis and structure of these and other aromatic polyesters may be described in more detail in U.S. Pat. Nos. 4,161,470; 4,473,682; 4,522,974; 4,375,530; 4,318,841;

4,256,624; 4,219,461; 4,083,829; 4,184,996; 4,279,803; 4,337,190; 4,355,134; 4,429,105; 4,393,191; 4,421,908; 4,434,262; and 5,541,240.

Liquid crystalline polyesteramides may likewise be obtained from (1) at least one aromatic hydroxycarboxylic acid and at least one aromatic aminocarboxylic acid; (2) at least one aromatic hydroxycarboxylic acid, at least one aromatic dicarboxylic acid, and at least one aromatic amine and/or diamine optionally having phenolic hydroxy groups; and (3) at least one aromatic dicarboxylic acid and at least one aromatic amine and/or diamine optionally having phenolic hydroxy groups. Suitable aromatic amines and diamines may include, for instance, 3-aminophenol; 4-aminophenol; 1,4-phenylenediamine; 1,3-phenylenediamine, etc., as well as alkyl, alkoxy, aryl and halogen substituents thereof. In one particular embodiment, the aromatic polyesteramide is derived from 2,6-hydroxynaphthoic acid, terephthalic acid, and 4-aminophenol. The monomer units derived from 2,6-hydroxynaphthoic acid may constitute from about 35% to about 85% of the polymer on a mole basis (e.g., 60%), the monomer units derived from terephthalic acid may constitute from about 5% to about 50% (e.g., 20%) of the polymer on a mole basis, and the monomer units derived from 4-aminophenol may constitute from about 5% to about 50% (e.g., 20%) of the polymer on a mole basis. In another embodiment, the aromatic polyesteramide contains monomer units derived from 2,6-hydroxynaphthoic acid, and 4-hydroxybenzoic acid, and 4-aminophenol, as well as other optional monomers (e.g., 4,4'-dihydroxybiphenyl and/or terephthalic acid). The synthesis and structure of these and other aromatic poly(esteramides) may be described in more detail in U.S. Pat. Nos. 4,339,375; 4,355,132; 4,351,917; 4,330,457; 4,351,918; and 5,204,443.

Meanwhile, the term "aramid polymer" refers to a class of polymers known as aromatic polyamides. Such polymers are typically prepared by the reaction between an amine group and a carboxylic acid halide group. Examples of suitable aramid polymers contemplated by the present invention include poly-metaphenylene isophthalamides and p-phenylene terephthalamides.

However, in order to achieve the desired abrasion resistance, it is to be understood that the additional polymer should be present in an amount of less than about 5 wt. % of the total weight of the sheath 104, such as in an amount of less than about 2.5 wt. % of the total weight of the sheath 104, such as in an amount of less than about 1 wt. % of the total weight of the sheath 104.

III. Applications

The braided structure of the present invention can be utilized in various medical applications. For instance, in some embodiments, the braided structure can be utilized as a suture material. Further, in other embodiments, the braided structure can be used as an actuation cable for a medical device. In addition, the braided structure can be used for any other application as known to one of skill in the art. For example, the braided structure can be used in load bearing orthopedic applications, artificial tendons/ligaments, device fixation, actuation cables, components for tissue repair, etc.

The present invention may be better understood by reference to the following example.

EXAMPLE

Several braided structures were formed as shown below in Table 1, included comparative examples C1a-C17 and examples 1a-4 and S1-S5, and the braided structures exhibited the physical and mechanical properties summarized in Table 1. Details as to the specific test procedures utilized to determine each property are set forth below.

Test Procedures

1. Sheath yarn twists per inch (TPI) was determined by using the direct untwist method on a hand driven twist tester
2. Braid diameter was determined by using a laser micrometer while a 30 gram weight was applied to the braided structure
3. Picks per inch (PPI) was determined by using an electronic measurement system while the braided structure was under magnification 4. Break load was determined by measuring the tensile force at which the braided structure failed using a universal mechanical testing system, with the tensile force being applied in the axial direction
5. Break load with 180° bend was determined by measuring the tensile force at which the braided structure failed while bent at 180° over a wire or pin having a diameter of 0.012 inches using a universal mechanical testing system
6. Ultimate tensile strength (UTS) was determined according to the following formula:

$$UTS = Break\ Load/(3.14 \times (radius\ of\ braided\ structure)^2)$$

7. Extension at Break was determined calculating the percent elongation of the braided structure at the point of failure using a universal mechanical testing system
8. Stiffness was determined according to the following formula:

$$Stiffness = Break\ Load/Extension\ at\ Break$$

9. Creep was calculated by determining the amount of elongation and percent of elongation of the braided structure. The braided structure was lopped around itself where both braid ends are parallel to one another in one testing grip to create a double braided structure. Using this double braided structure at a constant 5 pounds-force (about 22.2 Newtons) for about 15 minutes and at an about 19 inch (48.3 centimeter) gage length on a horn grip, then normalizing this value by multiplying the elongation of the braided structure at about 15 minutes by a set ratio longer than the test gage length vs. the test gage length
10. Abrasion resistance rankings of excellent, adequate, or poor were obtained based on the following: each sample braided structure was cycled 20 millimeters in a backwards direction and 20 millimeters in a forwards direction for a total of 40 cycles across a metal edge having a 1 millimeter radius with 200 grams of weight applied to the braided structure and the number of broken filaments in an inch of the braid was determined, where a ranking of excellent was given for braided structures with less than 10 broken filaments, a ranking of adequate was given for braided structures with between 10 and 50 broken filaments, and a ranking of poor was given for braided structures with more than 50 broken filaments

TABLE 1

| Sample | Sheath Yarn Description | Core Yarn Description | Diameter (Inches) | Picks Per Inch | Break Load (lbf) |
|---|---|---|---|---|---|
| C1a | 50 D LCP$^A$, 12 TPI S & Z | 100 D LCP TS$^H$ | 0.0104 | 28 | 19.15 |
| C1b | 50 D LCP$^A$, 12 TPI S & Z | 100 D LCP TS$^H$ | 0.0104 | 20 | 20.77 |
| C1c | 50 D LCP$^A$, 12 TPI S & Z | 100 D LCP TS$^H$ | 0.0104 | 38 | 15.46 |
| C2a | 50 D LCP$^A$, 12 TPI S & Z | 100 D UHMWPE$^J$ | 0.0110 | 28 | 20.27 |
| C2b | 50 D LCP$^A$, 12 TPI S & Z | 100 D UHMWPE$^J$ | 0.0110 | 20 | 22.34 |
| C2c | 50 D LCP$^A$, 12 TPI S & Z | 100 D UHMWPE$^J$ | 0.0110 | 38 | 15.74 |
| C3 | 50 D LCP$^A$, 12 TPI S & Z | 100 D UHMWPE$^K$ | 0.0100 | 28 | 19.51 |
| C4 | 50 D UHMWPE$^B$, 3 TPI S & Z | 100 D LCP$^H$ | 0.0115 | 20 | 23.44 |
| C5 | 50 D UHMWPE$^B$, 3 TPI S & Z | 50 D UHMWPE$^L$ | 0.0117 | 25 | 23.58 |
| C6 | 50 D LCP$^C$ Untwisted | 100 D LCP$^H$ | 0.0100 | 20 | 28.86 |
| C7 | 50 D LCP$^D$, 6.5 TPI S & Z | 100 D LCP$^H$ | 0.0107 | 20 | 21.83 |
| C8 | 50 D UHMWPE$^E$, 6.5 TPI S & Z | 100 D LCP$^H$ | 0.0118 | 20 | 25.36 |
| C9 | 50 D UHMWPE$^E$, 6.5 TPI S & Z | 100 D LCP$^H$ | 0.0118 | 14 | 27.47 |
| C10 | 50 D LCP$^C$ Untwisted | 100 D LCP$^H$ | 0.0099 | 14 | 28.82 |
| C11 | 30 D UHMWPE Untwisted$^M$ | 600 D Aramid | 0.0144 | 88 | 12.43 |
| C12 | 30 D UHMWPE Untwisted$^M$ | 800 D Aramid | 0.0159 | 88 | 16.37 |
| C13 | 30 D UHMWPE Untwisted$^M$ | 600 D Aramid | 0.0147 | 36 | 40.04 |
| C14 | 30 D UHMWPE Untwisted$^M$ | 600 D Aramid | 0.0147 | 46 | 34.62 |
| C15 | 30 D UHMWPE Untwisted$^M$ | 600 D Aramid | 0.0147 | — | 21.13 |
| C16 | 30 D UHMWPE Untwisted$^M$ | 400 D Aramid, 5 TPI | 0.0125 | 65 | 28.26 |
| C17 | 40 D PolyethyleneTerephthalate Untwisted$^N$ | 400 D Aramid, 5 TPI | 0.0126 | 54 | 22.65 |
| 1a | 50 D UHMWPE$^E$, 6.5 TPI S & Z | 100 D LCP$^I$ | 0.0116 | 20 | 18.25 |
| 1b | 50 D UHMWPE$^E$, 6.5 TPI S & Z | 100 D LCP$^I$ | 0.0116 | 28 | 18.38 |
| 1c | 50 D UHMWPE$^E$, 6.5 TPI S & Z | 100 D LCP$^I$ | 0.0116 | 38 | 19.55 |
| 2 | 50 D UHMWPE$^E$, 6.5 TPI S & Z | 100 D LCP$^I$ | 0.0119 | 14 | 20.17 |
| 3 | 50 D UHMWPE$^F$, 6.5 TPI S & Z | 100 D LCP$^I$ | 0.0117 | 20 | 22.23 |
| 4 | 50 D UHMWPE$^G$, 6.5 TPI S & Z | 100 D LCP$^I$ | 0.0116 | 20 | 26.19 |
| S1 | 30 D UHMWPE Untwisted$^M$ | 25 D LCP$^P$ | 0.0082 | 20 | 14.77 |
| S2 | 30 D UHMWPE Untwisted$^M$ | 25 D LCP$^P$ | 0.0229 | 20 | 52.15 |
| S3 | 30 D UHMWPE Untwisted$^M$ | 25 D LCP$^P$ | 0.0076 | 20 | 9.62 |
| S4 | 100 D UHMWPE Untwisted$^O$ | 25 D LCP$^P$ | 0.0142 | 20 | 32.15 |
| S5 | 50 D UHMWPE$^E$, 6.5 TPI S & Z | 25 D LCP$^P$ | 0.0110 | 20 | 21.50 |

(Columns Continued)

| Sample | Ultimate Tensile Strength (psi) | Break Load (lbf) 180° Bend | Extension at Break (%) | Stiffness (lbf/in.) | Creep (Inches) | Creep (% extension) | Abrasion Resistance |
|---|---|---|---|---|---|---|---|
| C1a | 2.26.E+05 | 17.16 | 3.2% | 37.32 | 0.028 | 0.15% | Poor |
| C1b | 2.45.E+05 | 17.75 | — | — | — | — | Poor |
| C1c | 1.82.E+05 | 18.89 | — | — | — | — | Poor |
| C2a | 2.13.E+05 | 17.79 | 3.2% | 39.20 | 0.039 | 0.21% | Poor |
| C2b | 2.35.E+05 | 21.92 | — | — | — | — | Poor |
| C2c | 1.66.E+05 | 18.81 | — | — | — | — | Poor |
| C3 | 2.48.E+05 | — | 3.0% | 40.64 | 0.030 | 0.16% | Poor |
| C4 | 2.26.E+05 | — | 6.8% | 21.87 | 0.090 | 0.47% | Excellent |
| C5 | 2.19.E+05 | — | 5.2% | 27.30 | 0.074 | 0.39% | Excellent |
| C6 | 3.68.E+05 | — | 3.8% | 46.33 | 0.215 | 1.13% | Poor |
| C7 | 2.43.E+05 | — | 3.6% | 37.65 | 0.127 | 0.67% | Poor |
| C8 | 2.32.E+05 | 26.54 | 6.0% | 27.37 | 0.314 | 1.65% | Excellent |
| C9 | 2.51.E+05 | 28.26 | 5.8% | 28.71 | 0.276 | 1.45% | Excellent |
| C10 | 3.75.E+05 | — | 3.6% | 48.68 | 0.190 | 1.00% | Poor |
| C11 | 7.64.E+04 | 18.13 | 2.1 | 49.77 | 0.084 | 0.44% | Adequate |
| C12 | 8.25.E+04 | 28.21 | 2.1 | 63.92 | 0.046 | 0.24% | Excellent |
| C13 | 2.36.E+05 | — | 5.6 | 59.26 | — | — | — |
| C14 | 2.04.E+05 | — | 5.1 | 58.00 | — | — | — |
| C15 | 1.25.E+05 | — | 2.9 | 62.34 | — | — | — |
| C16 | 2.30.E+05 | — | 4.5 | 52.72 | — | — | — |
| C17 | 1.82.E+05 | 23.76 | 3.8 | 49.19 | 0.046 | 0.24% | Poor |
| 1a | 1.73.E+05 | 18.63 | 4.1% | 27.52 | 0.230 | 1.21% | Excellent |
| 1b | 1.74.E+05 | 18.01 | — | — | — | — | Excellent |
| 1c | 1.85.E+05 | 24.73 | — | — | — | — | Excellent |
| 2 | 1.81.E+05 | 24.26 | 3.8% | 32.36 | 0.239 | 1.26% | Excellent |
| 3 | 2.07.E+05 | — | 2.3% | 58.95 | 0.164 | 0.86% | Excellent |
| 4 | 2.48.E+05 | — | 2.6% | 63.55 | 0.134 | 0.71% | Excellent |
| S1 | 2.80.E+05 | 19.98 | 3.7% | 27.75 | 0.470 | 2.47% | Excellent |
| S2 | 1.27.E+05 | 61.55 | 4.2% | 85.07 | 0.271 | 1.43% | Excellent |
| S3 | 2.12.E+05 | 15.07 | 3.2% | 20.72 | 0.542 | 2.85% | Excellent |
| S4 | 2.03.E+05 | 34.73 | 3.6% | 60.82 | 0.261 | 1.37% | Excellent |
| S5 | 2.26.E+05 | 24.74 | 3.3% | 34.93 | 0.335 | 1.76% | Excellent |

Explanation of Superscripts in Sheath Yarn Description and Core Yarn Description Columns:

A—45-55 denier; 24 filaments; 0.002467-0.002934 inch diameter; 2.3-3.1% elongation; 22-33 tenacity (g/denier); 990-1815 g max force; 11-13 TPI B—45-56 denier; 25 filaments; 0.003188-0.003557 inch diameter; 2-7% elongation; 22-47 tenacity (g/denier); 990-2632 g max force; 1-5 TPI C—47-55 denier; 24 filaments; 0.002521-0.002934 inch diameter; 3-4.5% elongation; 21.5-38.4 tenacity (g/denier); 1010.5-2113.1 g max force; 0 TPI D—45-55 denier; 24 filaments; 0.002521-0.002934 inch diameter; 3-5% elongation; 20-40 tenacity (g/denier); 900-2200 g max force; 5-9 TPI E—46-56 denier; 25 filaments; 0.003224-0.003557 inch diameter; 2-7% elongation; 25-45 tenacity (g/denier); 1150-2520 g max force; 5-9 TPI F—46-57 denier; 20 filaments; 0.003224-0.003588 inch diameter; 1.9-4.7% elongation; 28-48 tenacity (g/denier); 1288-2736 g max force; 5-9 TPI G—40-60 denier; 31-35 filaments; 0.003006-0.003682 inch diameter; 1.3-5% elongation; 37.4-50.6 tenacity (g/denier); 1496-3036 g max force; 5-9 TPI H—94-105 denier; 48 filaments; 0.003566-0.004054 inch diameter; 2.5-4.5% elongation; 22-36 tenacity (g/denier); 2068-3780 g max force; 0 TPI I—96-105 denier; 48 filaments; 0.003604-0.004054 inch diameter; 2.1-2.5% elongation; 21-28 tenacity (g/denier); 2016-2940 g max force; 0 TPI J—90-110 denier; 40-48 filaments; 0.004509-0.004985 inch diameter; 2.1-4.5% elongation; 28.5-41.2 tenacity (g/denier); 2565.9-4535.3 g max force; 0 TPI K—92-114 denier; 40 filaments; 0.004559-0.005075 inch diameter; 1.9-4.7% elongation; 28-48 tenacity (g/denier); 2576-5472 g max force; 0 TPI L—45-56 denier; 25 filaments; 0.003188-0.003557 inch diameter; 2.3-4.5% elongation; 28-40 tenacity (g/denier); 1260-2240 g max force; 0 TPI M—25-35 denier; 16 filaments; 0.00303-0.00403 inch diameter; 2-5% elongation; 20-55 tenacity (g/denier); 650-1700 g max force; 0 TPI N—35-45 denier; 27 filaments; 0.002357-0.002673 inch diameter; 19-45% elongation; 3.8-5.2 tenacity (g/denier); 130-235 g max force, 0 TPI O—80-120 denier; 41 filaments; 0.004251-0.00520658 inch diameter; 2.5-4.5% elongation; 25-45 tenacity (g/denier); 2500-4500 g max force; 0 TPI P—21-29 denier; 6 filaments; 0.001839-0.00220275 inch diameter; 3-5% elongation; 20-40 tenacity (g/denier); 600-950 g max force

DISCUSSION

As shown above in Table 1, which summarizes the various braided structures and their resulting physical and mechanical properties, although comparative samples C1 through C17 had the small diameter required for the braided structure for use in medical applications, none of the comparative samples C1 through C17 exhibited the most preferred mechanical properties across all categories. For instance, comparative samples C4, C8, C9, and C13 exhibited high extension at break percentages, C11 and C12 exhibited low ultimate tensile strengths, and samples C1a, C1b, C1c, C2a, C2b, C2c, C3, C6, C7, C10, C11, and C17 exhibited poor abrasion resistance as evidenced by fraying of the braided structure after cycling the braided structure 20 millimeters in a backwards direction and 20 millimeters in a forwards direction for a total of 40 cycles across a metal edge having a 1 millimeter radius with 200 grams of weight applied to the braided structure.

On the other hand, surprisingly, the specific arrangement of the braided structures of samples 1a, 1b, 1c, 2, 3, and 4 and samples S1, S2, S3, S4, and S5 were abrasion resistant, exhibited high loads at break in the normal and 180° bend testing configurations, exhibited low extension at break, exhibited increased stiffness, and had low creep values, all while having a small diameter suitable for use in suture or actuation cable applications and maintaining a high ultimate tensile strength ranging from $1.27 \times 10^5$ pounds per square inch (about 876 megapascals) to $2.80 \times 10^5$ pounds per square inch (about 1930 megapascals). In another aspect, the braided structure can exhibit an ultimate tensile strength ranging from about 15 grams/denier yarn to about 35 grams/denier yarn.

Figure 3:
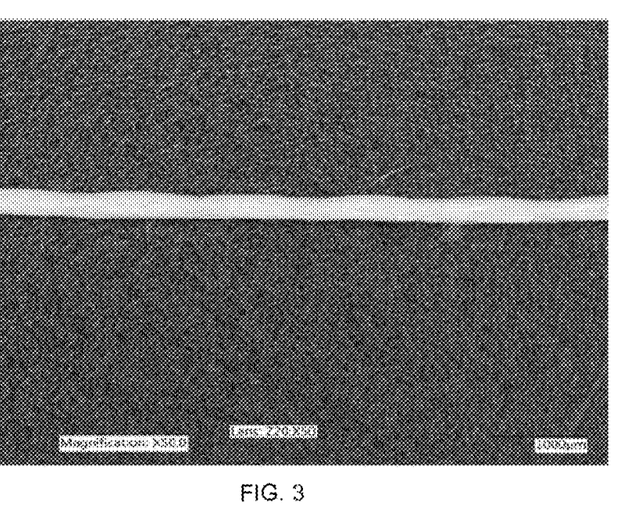
FIG. 3 is a photograph of a comparative example braided structure having a liquid crystalline polymer sheath after 5 abrasion testing cycles.
Figure 4:
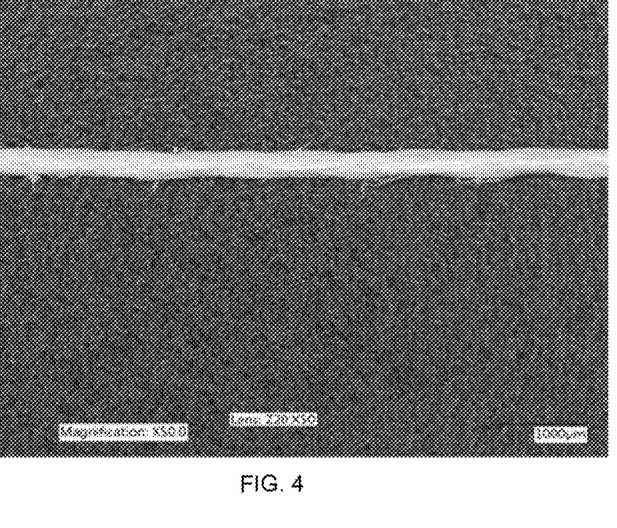
FIG. 4 is a photograph of a comparative example braided structure having a liquid crystalline polymer sheath after 10 abrasion testing cycles.
Figure 5:
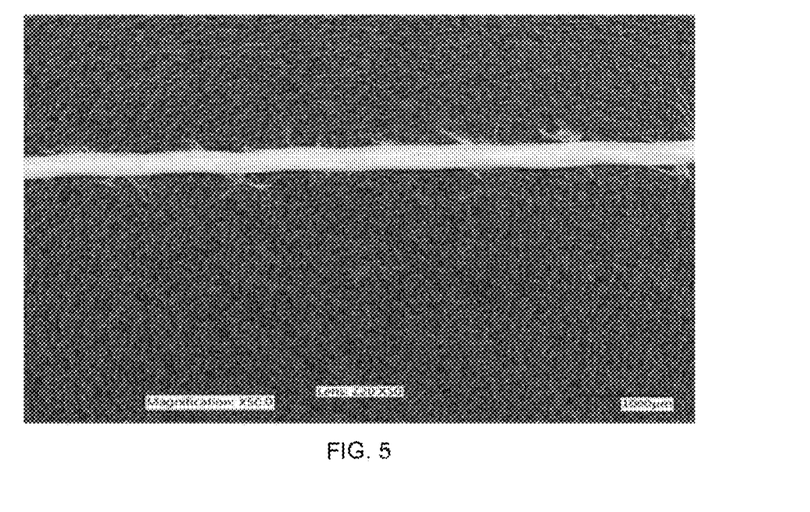
FIG. 5 is a photograph of a comparative example braided structure having a liquid crystalline polymer sheath after 20 abrasion testing cycles.
Figure 6:
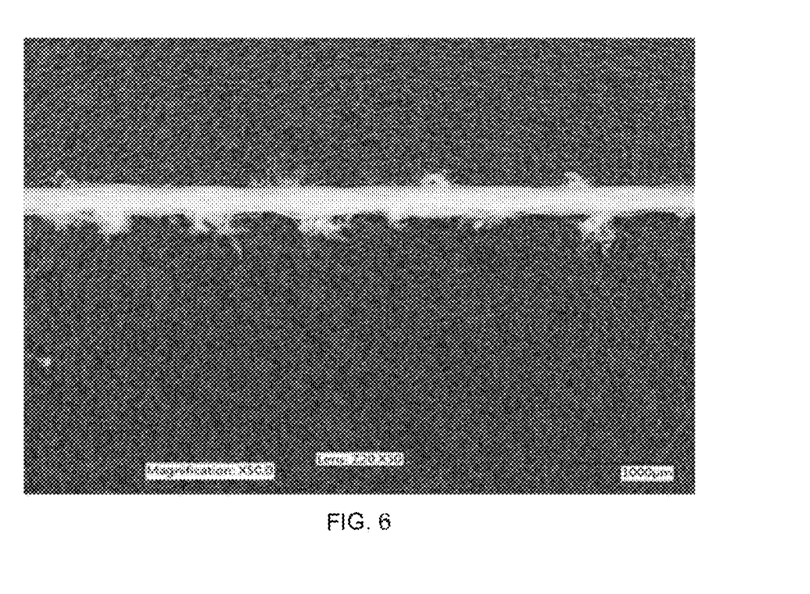
FIG. 6 is a photograph of a comparative example braided structure having a liquid crystalline polymer sheath after 40 abrasion testing cycles.

FIGS. 3-10 will now be discussed in more detail to demonstrate the improved abrasion resistance of the braided structure of the present invention compared to other braided structures. Specifically, FIG. 3 is a photograph of a braided structure having a liquid crystalline polymer sheath as in comparative examples C1a-C3, C6-C7, and C10 after cycling the braided structure 20 millimeters in a backwards direction and 20 millimeters in a forwards direction for a total of 5 cycles across a metal edge having a 1 millimeter radius with 200 grams of weight applied to the braided structure; FIG. 4 is a photograph of a braided structure having a liquid crystalline polymer sheath as in comparative examples C1a-C3, C6-C7, and C10 after cycling the braided structure 20 millimeters in a backwards direction and 20 millimeters in a forwards direction for a total of 10 cycles across a metal edge having a 1 millimeter radius with 200 grams of weight applied to the braided structure; FIG. 5 is a photograph of a braided structure having a liquid crystalline polymer sheath as in comparative examples C1a-C3, C6-C7, and C10 after cycling the braided structure 20 millimeters in a backwards direction and 20 millimeters in a forwards direction for a total of 20 cycles across a metal edge having a 1 millimeter radius with 200 grams of weight applied to the braided structure; and FIG. 6 is a photograph of a braided structure having a liquid crystalline polymer sheath as in comparative examples C1a-C3, C6-C7, and C10 after cycling the braided structure 20 millimeters in a backwards direction and 20 millimeters in a forwards direction for a total of 40 cycles across a metal edge having a 1 millimeter radius with 200 grams of weight applied to the braided structure. As shown, even after only 5 cycles, the braided structure as in comparative examples C1a-C3, C6-C7, and C10 exhibits fraying, which is even far more pronounced after 40 cycles, indicating that the braided structures of comparative examples C1a-C3, C6-C7, and C10 lack abrasion resistance.

Figure 7:
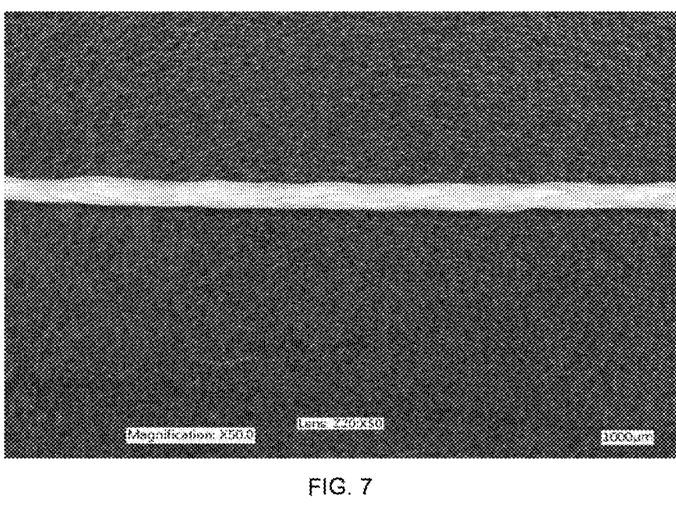
FIG. 7 is a photograph of a braided structure of the present invention having an ultra-high molecular weight polyethylene polymer sheath after 5 abrasion testing cycles.
Figure 8:
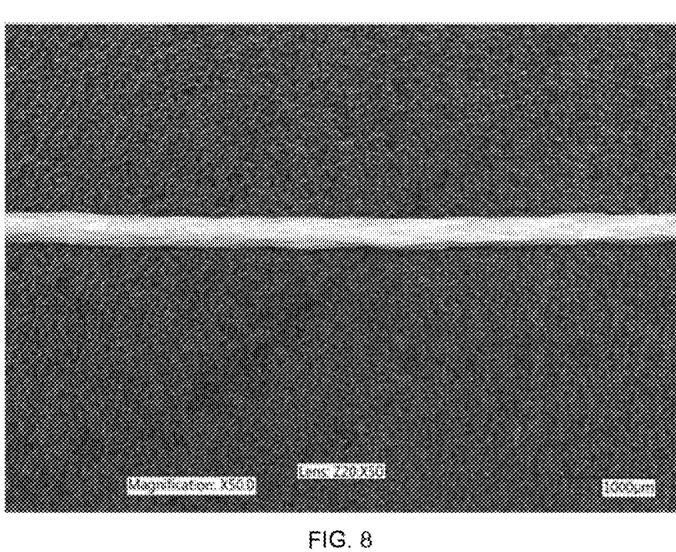
FIG. 8 is a photograph of a braided structure of the present invention having an ultra-high molecular weight polyethylene polymer sheath after 10 abrasion testing cycles.

On the other hand, FIG. 7 is a photograph of a braided structure having an ultra high molecular weight polyethylene polymer sheath as in examples 1a-4 and S1-S5 after cycling the braided structure 20 millimeters in a backwards direction and 20 millimeters in a forwards direction for a total of 5 cycles across a metal edge having a 1 millimeter radius with 200 grams of weight applied to the braided structure; FIG. 8 is a photograph of a braided structure having an ultra high molecular weight polyethylene polymer sheath as in examples 1a-4 and S1-S5 after cycling the braided structure 20 millimeters in a backwards direction and 20 millimeters in a forwards direction for a total of 10 cycles across a metal edge having a 1 millimeter radius with 200 grams of weight applied to the braided structure; FIG.

Figure 9:
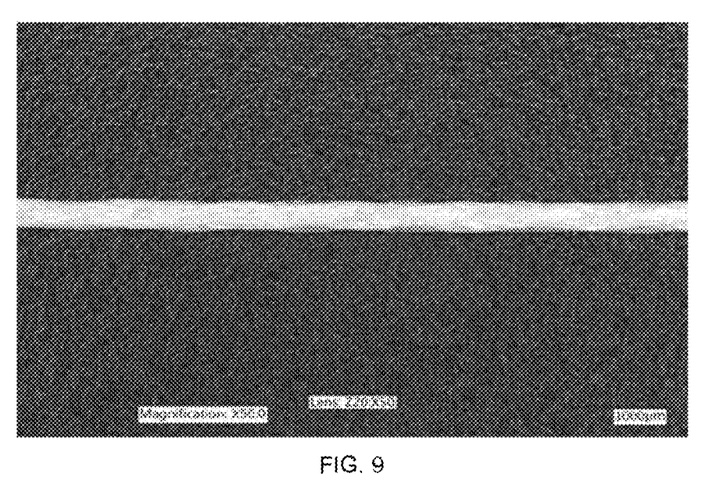
FIG. 9 is a photograph of a braided structure of the present invention having an ultra-high molecular weight polyethylene polymer sheath after 20 abrasion testing cycles.
Figure 10:
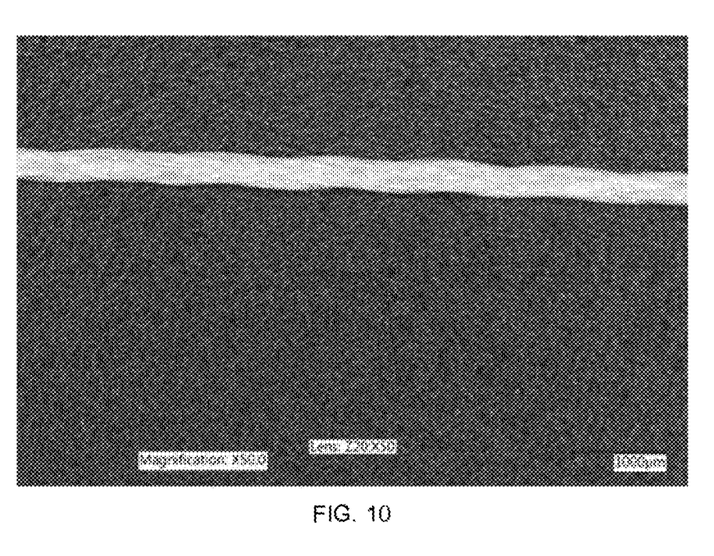
FIG. 10 is a photograph of a braided structure of the present invention having an ultra-high molecular weight polyethylene polymer sheath after 40 abrasion testing cycles.

9 is a photograph of a braided structure having an ultra high molecular weight polyethylene polymer sheath as in examples 1a-4 and S1-S5 after cycling the braided structure 20 millimeters in a backwards direction and 20 millimeters in a forwards direction for a total of 20 cycles across a metal edge having a 1 millimeter radius with 200 grams of weight applied to the braided structure; and FIG. 10 is a photograph of a braided structure having an ultra high molecular weight polyethylene polymer sheath as in examples 1a-4 and S1-S5 after cycling the braided structure 20 millimeters in a backwards direction and 20 millimeters in a forwards direction for a total of 40 cycles across a metal edge having a 1 millimeter radius with 200 grams of weight applied to the braided structure. As shown, even after 40 cycles, the braided structures as in examples 1a-4 and S1-S5 show no fraying, indicating the braided structures of the present invention are abrasion resistant.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A braided structure comprising:
   a core comprising at least one yarn, wherein the at least one yarn comprises an aromatic polymer, and wherein a linear mass density of the core ranges from about 8 denier to about 125 denier; and
   a sheath braided around the core, wherein the sheath comprises a plurality of ultra-high molecular weight polyolefin yarns, wherein the braided structure has an overall diameter ranging from about 60 micrometers to about 650 micrometers.

2. The braided structure of claim 1, wherein the aromatic polymer comprises a liquid crystalline polymer, an aramid polymer, or a combination thereof.

3. The braided structure of claim 1, wherein the sheath comprises from 2 yarns to about 48 yarns and each of the plurality of yarns in the sheath comprises from 1 filament to about 72 filaments.

4. The braided structure of claim 1, wherein the at least one yarn in the core comprises from about 3 filaments to about 96 filaments.

5. The braided structure of claim 1, wherein the ultra-high molecular weight polyolefin comprises an ultrahigh molecular weight polyethylene having a weight average molecular weight (Mw) of at least about 500,000 grams/mole (g/mol).

6. The braided structure of claim 1, wherein the braided structure exhibits a creep of less than 8 percent elongation after about 15 minutes.

7. The braided structure of claim 1, wherein the braided structure exhibits resistance to abrasion after cycling the braided structure 20 millimeters in a backwards direction and 20 millimeters in a forwards direction for a total of 40 cycles across a metal edge having a 1 millimeter radius with 200 grams of weight applied to the braided structure, wherein the braided sheath comprises a plurality of filaments, and wherein the braided structure includes less than 50 broken filaments per linear inch after cycling.

8. The braided structure of claim 1, wherein the braided structure exhibits a load at break ranging from about 5 pounds-force (about 22.2 Newtons) to about 60 pounds-force (about 266.9 Newtons).

9. The braided structure of claim 1, wherein the braided structure exhibits an extension at break ranging from about 2% to about 5.5%.

10. The braided structure of claim 1, wherein the braided structure exhibits a stiffness ranging from about 10 pounds-force per inch (about 1.75 Newtons/millimeter) to about 90 pounds-force per inch (about 15.8 Newtons/millimeter).

11. The braided structure of claim 1, wherein the braided structure exhibits an ultimate tensile strength ranging from about $8.0 \times 10^4$ pounds per square inch (about 550 megapascals) to about $3.9 \times 10^5$ pounds per square inch (about 2710 megapascals).

12. The braided structure of claim 1, wherein the braided structure comprises from about 10 picks per inch (PPI) to about 90 picks per inch (PPI).

13. The braided structure of claim 1, wherein the plurality of ultra-high molecular weight polyolefin yarns comprises from 0 twists per inch (TPI) to about 12 twists per inch (TPI).

14. The braided structure of claim 1, wherein the at least one yarn in the core comprises zero twists per inch (TPI) to about 2 twists per inch (TPI).

15. The braided structure of claim 1, wherein each of the plurality of yarns in the sheath has a linear mass density ranging from about 8 denier to about 125 denier.

16. The braided structure of claim 1, wherein the core has an overall diameter ranging from about 30 micrometers to about 333 micrometers.

17. The braided structure of claim 1, wherein the aromatic polymer comprises a liquid crystalline polymer.

18. The braided structure of claim 1, wherein the ultra-high molecular weight polyolefin is ultrahigh molecular weight polyethylene and each of the plurality of yarns in the sheath has a linear mass density ranging from about 8 denier to about 125 denier.

19. An actuation cable for a medical device, a suture, a load bearing orthopedic application, an artificial tendon or ligament, a component for tissue repair, an actuation cable, or a fixation device comprising the braided structure of claim 1.

20. A braided structure comprising:
   a core comprising at least one yarn, wherein the at least one yarn comprises an aromatic polymer, wherein a linear mass density of the core ranges from about 8 denier to about 125 denier; and
   a sheath braided around the core, wherein the sheath comprises a plurality of ultra-high molecular weight polyolefin yarns, wherein the braided structure exhibits resistance to abrasion after cycling the braided structure 20 millimeters in a backwards direction and 20 millimeters in a forwards direction for a total of 40 cycles across a metal edge having a 1 millimeter radius with 200 grams of weight applied to the braided structure, wherein the braided sheath comprises a plurality of filaments, and wherein the braided structure includes less than 50 broken filaments per linear inch after cycling.

21. A braided structure comprising:
   a core comprising at least one yarn, wherein the at least one yarn comprises an aromatic polymer, wherein a linear mass density of the core ranges from about 8 denier to about 125 denier; and a sheath braided around the core, wherein the sheath comprises a plurality of ultra-high molecular weight polyolefin yarns, wherein the braided structure exhibits a creep of less than about 8 percent elongation after about 15 minutes.

22. A braided structure comprising:

a core comprising at least one yarn, wherein the at least one yarn comprises a liquid crystalline polymer, wherein a linear mass density of the core ranges from about 8 denier to about 125 denier; and a sheath braided around the core, wherein the sheath comprises a plurality of ultra-high molecular weight polyolefin yarns, wherein the braided structure has an overall diameter ranging from about 60 micrometers to about 650 micrometers.

* * * * *